United States Patent [19]

Francis

[11] 3,993,048
[45] Nov. 23, 1976

[54] BIOMEDICAL ELECTRODE
[75] Inventor: Howard T. Francis, Park Forest, Ill.
[73] Assignee: Biomedical International Company, River Grove, Ill.
[22] Filed: Sept. 8, 1972
[21] Appl. No.: 287,562

[52] U.S. Cl. .......................... 128/2.06 E; 128/2.1 E; 128/417; 128/DIG. 4; 204/195 B
[51] Int. Cl.² .......................................... A61B 5/04
[58] Field of Search ....... 128/2.06 E, 2.1 E, DIG. 4, 128/417, 418, 404, 405, 410, 411, 416; 204/195 B, 195 F, 195 G, 195 H, 195 L, 195 M

[56] References Cited
UNITED STATES PATENTS

| | | | |
|---|---|---|---|
| 3,295,515 | 1/1967 | Kahn | 128/DIG. 4 X |
| 3,438,886 | 4/1969 | Ross | 204/195 L |
| 3,448,032 | 6/1969 | Settzo et al. | 204/195 L |
| 3,486,997 | 12/1969 | Peterson | 204/195 F |
| 3,496,929 | 2/1970 | Domingues | 128/DIG. 4 X |
| 3,498,289 | 3/1970 | Watanabe et al. | 128/DIG. 4 |
| 3,598,713 | 8/1971 | Baum et al. | 204/195 L |

FOREIGN PATENTS OR APPLICATIONS
216,902   8/1966   U.S.S.R. ............. 128/2.1 E

*Primary Examiner*—Robert W. Michell
*Assistant Examiner*—Lee S. Cohen
*Attorney, Agent, or Firm*—Anthony S. Zummer

[57] ABSTRACT

An electrode is provided for medical and biological use. The electrode is a calomel type electrode having a housing, with a mercury-calomel saline solution junction in the housing. A cellophane diaphragm is mounted on the housing to retain the saline solution. However, the diaphragm is sufficiently permeable to allow ionic conduction between a surface of a body being tested and the saline solution.

5 Claims, 5 Drawing Figures

BIOMEDICAL ELECTRODE

BACKGROUND OF THE INVENTION

Electrical measurements have become quite prevalent in medical and biomedical testing, and are used for monitoring a wide variety of functions of the human body. Some of these measurements are used in electrocardiograms, electroencephalograms and electromyograms. In order to make an electrical measurement, it is necessary to have a good electrical contact with the body to be measured through an electrode which is part of a half cell and is connected to a measuring apparatus.

It is recognized that a good electrode has certain important characteristics, such as, low impedance and stability. Since the electrode operates as a half cell, the half cell potential must be as stable as possible, with no influence on the half cell by perspiration or movement of the patient. The ultimate purpose of the electrode is the faithful transmission of the physiologically-generated electrical signal from the patient's skin to the recording and/or observing apparatus.

When the heretofore known electrode is used on a human body, it is necessary to prepare the area of the skin upon which the electrode is to be positioned. Typically, the skin is first cleaned; and then it is often abraded to provide a good electrical contact surface. The abrasion removes dead skin, which may impede the proper transmittal of an electrical signal to the electrode. A suitable electrolyte, generally in a gel form, is placed on the patient's skin. The electrode is then placed on the gel, forming a half cell, so that physiologically-generated electrical signals are observable. The electrical signal is carried to an amplifier and a recording and/or observing apparatus.

A very popular electrode construction which is commonly in use is one which utilizes a silver-silver chloride-chloride ion half cell. The silver-silver chloride-chloride ion half cell is generally formed either by compressing a mixture of silver and silver chloride powders and placing the compressed mixture in contact with a suitable electrolyte, or by forming a half cell by first electrochemically converting a surface of a silver piece to a silver chloride layer and placing a silver chloride layer into contact with an electrolyte.

These known electrodes generally have performed satisfactorily in many applications. However, these electrodes have certain undesirable properties. The electrolyte which is placed in contact with a patient's skin is generally in a gel form or a paste form. The paste is messy to handle, both for the operator and for the patient. The preparation technique causes irritation to the patient, especially when the skin is abraded for a good electrical contact. When prolonged readings are to be taken, the paste tends to dry, causing the impedance to increase at the electrode skin interface, thereby changing the observed signal by virtue of the failure to make a faithful transmission of the physiologically-generated signal. Furthermore, the electrical characteristics of these electrodes vary from electrode to electrode, so that there must be matching of electrodes and the measurements are limited to an AC amplifier. A DC amplifier is desirable in taking certain measurements, and particularly for electroencephalograms. The electrodes drift as the potential of the half cell changes in an erratic manner in relation to time. This often causes errors in measurement of signals and thereby gives a distorted view of the physiological signal-generating organ or body portion. A further problem which accompanies the known electrodes is that silver chloride cannot be kept in contact with a patient's skin for any prolonged time without causing irritation due to silver migration. Thus, prolonged continuous readings cannot be taken without subjecting the patient to tissue injury.

SUMMARY OF THE INVENTION

The present electrode does not use a paste or gel between a body surface and the electrode. It is an "isotonic calomel" electrode, utilizing a mercury-calomel admixture in contact with an isotonic saline solution. The electrolyte is a saline solution contained in a housing, with a cellophane diaphragm on one side of the housing retaining the electrolyte in the housing. The cellophane diaphragm is placed on the surface of a patient's skin, providing an ionic contact between the patient's skin and the electrode. The electrical half cell potential of the electrode is defined by the mercury-mercurous ion reaction. It is important to note that the electrical half cell is completely sealed, except for the ion conductive diaphragm, so that the electrolyte is isolated and there is no effect upon the half cell by motion or exterior chemicals. The potential of the half cell is determined by the chloride ions in the electrolyte, which defines the mercury-mercurous ion reaction. Even shaking the electrode does not change the concentration. Thus, the effect of motion of the electrode is nil; and, of course, motion of the electrolyte saline solution has no effect upon the electrical potential. The cellophane diaphragm is put into electrical contact with the skin of a patient as soon as the diaphragm touches the skin. Since the solution behind the diaphragm is an isotonic saline solution, there is no irritation to the skin. The cellophane diaphragm is itself non-toxic, thereby creating no problems.

DESCRIPTION OF THE PREFERRED EMBODIMENT

Figure 1:
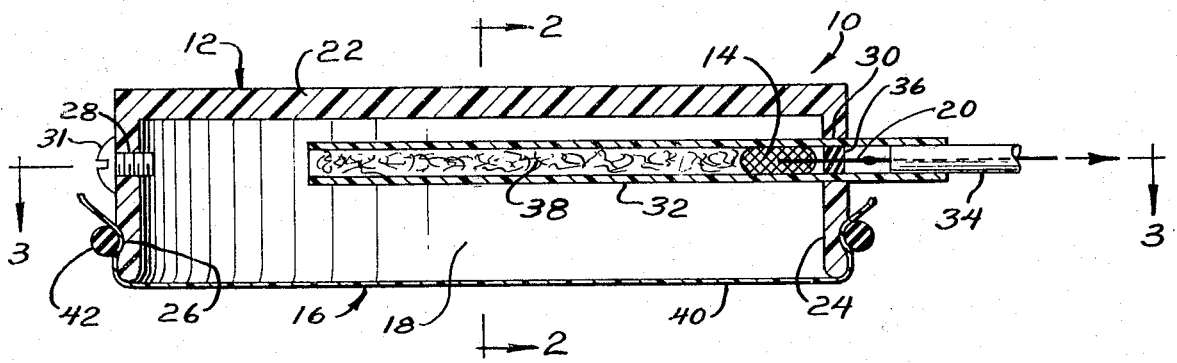
FIG. 1 is a cross-sectional view of an electrode embodying the present invention.
Figure 2:
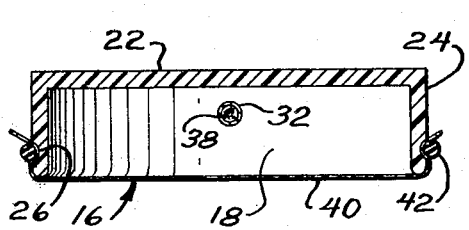
FIG. 2 is a cross-sectional view taken on Line 2—2 of FIG. 1.
Figure 3:
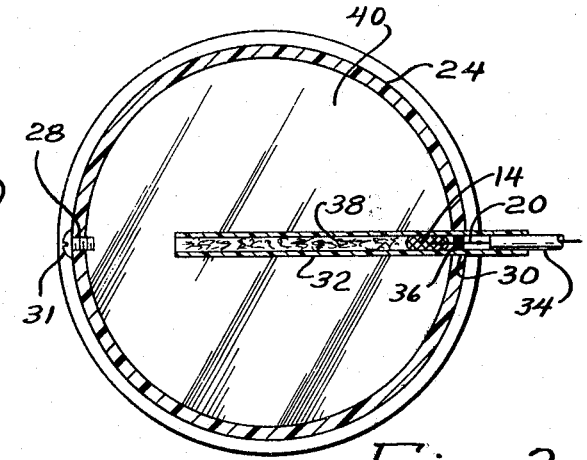
FIG. 3 is a cross-sectional view taken on Line 3—3 of FIG. 2.

Referring now to the drawings, and especially to FIG. 1, an electrode which is a specific embodiment of the instant invention is a mercury calomel half cell and is generally indicated by numeral 10. The electrode 10 generally includes a housing 12, a mercury calomel mixture 14 in the housing, a diaphragm 16 mounted on the housing, and an electrolyte 18 held in the housing 12 by the diaphragm 16 and contacting the mercury calomel mixture 14. A platinum lead wire 20 is connected to the mercury calomel mixture 14.

The housing 12 is made of lucite and has a circular top 22, with a cylindrical wall 24 formed integral with the outer periphery of the top. A sealing groove 26 is formed in the cylindrical wall 24 adjacent to the open end thereof. The cylindrical wall has a threaded filling aperture 28 on one side and an electrical port 30 opposite to the filling aperture 28. A screw plug 31 is positioned in the filling aperture 28 to seal closed the aperture.

A non-conductive tube 32 is positioned in port 30 and fixed therein. Tube 32 extends radially inward of the cylindrical wall 24 to be aligned with the filling aperture 28 so that the tube may be filled with electrolyte by use of a syringe to eliminate air bubbles. The mercury calomel mixture 14 is positioned in the tube adjacent to the cylindrical wall 24. In this instance, the mercury calomel mixture is 50% mercury and 50% mercurous chloride by weight, although it is readily apparent that other suitable and well-known proportions may be used for the mercury calomel mixture. The lead wire 20 has one end positioned in the mercury calomel mixture. The other end of wire 20 is connected to a conventional insulated copper wire 34 to provide an electrical conductor from the mercury calomel mixture exteriorly of the housing 12. A seal 36 is positioned in the tube and surrounds a portion of the wire 20, thereby preventing the mercury calomel mixture from flowing out of the housing through the tube. Glass wool 38 is packed loosely in the other end of the tube to prevent the mercury calomel mixture from leaving the tube through the other end; but the glass wool is sufficiently loose to allow the electrolyte to contact the mercury calomel mixture.

In this specific embodiment of the invention, the electrolyte 18 is an isotonic physiological saline solution of nine grams of sodium chloride per liter of water. The saline solution has free chloride ions for defining the mercury-mercurous ion reaction in the half cell. The saline solution does not completely fill the housing, but rather a small air pocket is provided. The small air pocket provides "give" to the diaphragm so that the diaphragm accommodates itself to a surface contact. The diaphragm 16 includes a sheet of cellophane 40 which covers the open end of the housing 12. The cellophane sheet 40 is held in place by a conventional rubber O-ring 42, which rests in the groove 26. The O-ring 42 is sufficiently tight so that the electrolyte does not leak between the wall 24 and the cellophane sheet 40.

The electrode 10 is connected to an appropriate amplifier and recording instrument in a well-known manner by means of an electrical conductor, i.e., the copper wire 34. The electrical apparatus is not shown herein since it is well-known in the art, but it may be a device such as a Hewlett-Packard 1511A electrocardiograph. The electrode 10 is placed on the skin of a patient and is held there by any appropriate means, such as, surgical adhesive tape.

A second and third electrode are also appropriately placed on a patient, as is well-known in the art. The second and third electrodes are also held in position by surgical adhesive tape. The second and third electrodes are also connected to the electrocardiogram machine. Additional electrodes may also be placed on the patient and appropriately connected to the machine, depending upon the particular application. The physiological electrical potential between two areas of the body is detected by the electrode and transmitted to the electrocardiogram machine. It is important to note that even though the electrode is secured to a patient and subjected to motion, this motion produces no effect on the electrode in view of the fact that the potential is determined solely by the chloride ion concentration in the electrolyte. It should further be noted that there is substantially no DC offset between electrode pairs. Freedom from DC offset and half cell stability facilitates measurements with a DC amplifier when desired. Since the electrode is held in contact with the patient's skin without the use of a paste or gel, as is conventional, there is no paste or gel to dry out, causing impedance changes and attendant deterioration of signal quality. Inasmuch as the electrode is held on a person's skin, the patient may perspire slightly under the electrode. This perspiration does not impede the operation of the electrode.

Figure 4:
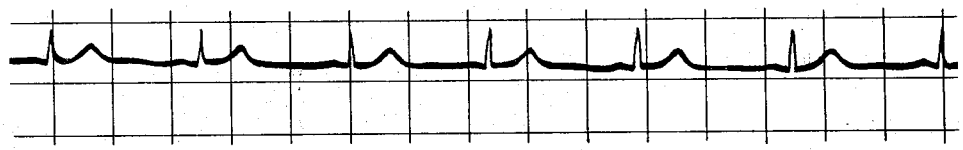
FIG. 4 is a copy of a graph, showing a representative readout using the subject electrode.
Figure 5:
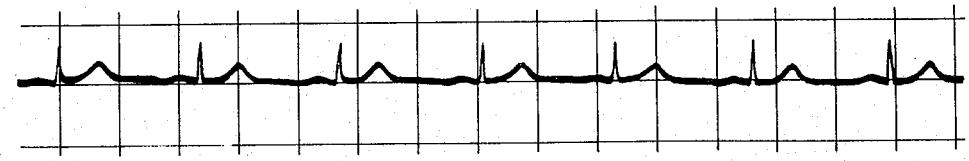
FIG. 5 is a copy of a graph, showing a representative readout using a prior art electrode.

The electrode 10 without a paste or gel between the electrode and a patient gives the same results as a conventional electrode with paste, clearly showing that the electrode 10 eliminates all of the problems associated with a paste and provides the advantages mentioned above. Electrode 10 and two other identical electrodes were attached to a patient with surgical adhesive tape in the usual locations on a patient. The electrodes were connected to a 1511A electrocardiogram manufactured by Hewlett-Packard of Waltham, Massachusetts, in the configuration known as "Lead I", and the results were recorded. A copy of the results is shown at FIG. 4. Three Welsh electrodes manufactured by Bowen & Co., Inc., of Bethesda, Maryland, were attached to the same patient at the same locations. A conventional paste was applied to the patient in conjunction with the Welsh electrodes. The Welsh electrodes were connected in the same configuration, and a copy of the results is shown in FIG. 5. Comparison of the electrocardiograms clearly demonstrates that, for short-run readings, there is no difference between the use of a conventional electrode with paste and electrode 10 without any paste. The advantages of the electrode 10 are accentuated in a long-run observation.

Although a specific embodiment of the herein-disclosed invention has been shown and described in detail above, it is to be understood that one skilled in the art may make various and sundry modifications without departing from the spirit and scope of the present invention. The present invention is limited only by the appended claims.

What is claimed is:

1. A biomedical electrode for taking electrical measurements of electrical signals physiologically generated by a subject, comprising, an electrical conductor adapted for connection to an instrument for making electrical measurements, a mercury calomel mixture connected to the electrical conductor, a solution of physiological saline contacting the mercury calomel mixture, and a flexible membrane retaining the solution of physiological saline and being wetted by said solution, said membrane being adapted for direct contact with a surface of the subject to allow ionic conductance through the membrane between the surface and the solution of physiological saline.

2. A biomedical electrode for taking electrical measurements of electrical signals physiologically generated by a subject as defined in claim 1 wherein said membrane is a sheet of cellophane.

3. A biomedical electrode for taking electrical measurements of electrical signals physiologically generated by a subject as defined in claim 1, including a housing holding the mercury calomel mixture and the solution of physiological saline, said membrane being mounted over an opening in one side of the housing to retain the solution of physiological saline in the housing.

4. A biomedical electrode for taking electrical measurements of electrical signals physiologically generated by a subject as defined in claim 3, including a pocket of air in the housing to allow the membrane to conform to a surface.

5. A biomedical electrode for taking electrical measurements of electrical signals physiologically generated by a subject as defined in claim 3 wherein the membrane is a sheet of cellophane.

* * * * *